United States Patent [19]

Tytgat et al.

[11] 4,160,948
[45] Jul. 10, 1979

[54] MONITORING EFFECTS OF A LIQUID ON METALLIC INSTALLATIONS

[75] Inventors: Daniel Tytgat, Brussels; Albert Degols, Berg, both of Belgium

[73] Assignee: Solvay & Cie., Brussels, Belgium

[21] Appl. No.: 855,388

[22] Filed: Nov. 28, 1977

[30] Foreign Application Priority Data

Nov. 26, 1976 [FR] France .................................. 76 35990

[51] Int. Cl.² .................................................. G01R 27/26
[52] U.S. Cl. .......................... 324/61 P; 324/65 CR; 324/71 E; 204/195 C; 23/230 C
[58] Field of Search ............. 324/61 P, 57 R, 65 CR, 324/71 E; 204/1 C, 195 C; 23/230 C, 253 C; 73/86

[56] References Cited

U.S. PATENT DOCUMENTS

| | | | |
|---|---|---|---|
| 3,418,848 | 12/1968 | Schaschl | 324/65 CR |
| 3,419,801 | 12/1968 | Cohn | 324/61 P |
| 3,612,998 | 10/1971 | Turner | 324/71 E X |
| 3,660,249 | 5/1972 | Townsend | 204/1 C |
| 3,716,460 | 2/1973 | Weisstuch et al. | 204/1 C |
| 3,757,210 | 9/1973 | Hansen et al. | 324/65 CR X |
| 3,948,744 | 4/1976 | Cushing | 204/195 C |
| 3,980,542 | 9/1976 | Winslow, Jr. | 324/65 CR X |
| 3,996,124 | 12/1976 | Eaton et al. | 324/65 CR X |
| 4,019,133 | 4/1977 | Manley et al. | 324/65 CR |

Primary Examiner—Stanley T. Krawczewicz
Attorney, Agent, or Firm—Spencer & Kaye

[57] ABSTRACT

The corrosive, erosive and/or encrusting effects of a liquid on metal surfaces are monitored by immersing a metallic probe into the liquid, and measuring simultaneously both the differential capacitance of the double layer between the probe and the liquid and the resistance between the probe and an auxiliary electrode, which are representative of the surface condition of the probe.

18 Claims, 7 Drawing Figures

MONITORING EFFECTS OF A LIQUID ON METALLIC INSTALLATIONS

BACKGROUND OF THE INVENTION

The present invention relates to a process and a device for monitoring the corrosive, erosive and/or encrusting nature of a liquid with respect to a metallic installation, such as, for example, a pipeline or a heat exchanger.

In handling a liquid in a metallic installation, there is sometimes the risk that the latter will suffer corrosion, erosion and/or local encrusting which can sooner or later interfere with the proper functioning of the installation. It is difficult to predict the appearance and development of these simultaneous phenomena of corrosion, erosion and encrusting of metallic installations, because they depend on a large number of factors, particularly the nature of the liquid treated, the possible presence of solid matter suspended in the treated liquid, the temperature, velocity and degree of turbulence of the liquid in the vicinity of the wall of the installation, the nature of the metal of the installation, the shape of the installation and its surface condition, especially its roughness.

Thus, in the presence of hard water, progressive furring, or scale formation, is generally observed in such installations; this furring, or scaling, which is particularly severe in the case of hot water, leads to progressive blockage of the installations and to a decrease in the efficiency of the heat exchangers.

In the presence of corrosive water such as softened water, there is furthermore the danger that installations made of stainless steel or galvanized steel can undergo local corrosion which can sometimes lead to perforation of the wall of the installation.

If the treated liquids contain solid materials in suspension, a local erosion of the walls of the installation, or a sedimentation in the zones of the installation where the liquid undergoes a sudden pressure drop, such as in enlargements of pipelines, or in bends, is sometimes observed.

Erosion or sedimentation phenomena can in particular occur in installations through which viscous liquids, such as slurries, flow, or in evaporators/crystallizers such as those commonly used for the treatment of aqueous solutions of sodium hydroxide originating from sodium chloride brine electrolysis cells.

It is known to utilize gravimetric methods of measurement to monitor the corrosive or encrusting character of liquids circulating in installations; as disclosed for example in the periodical *Materials Protection*, October 1962, at pages 10 to 19 and 27. These known methods consist of periodically withdrawing from the liquid a probe which is normally immersed therein, descaling the probe so as to remove materials which may be encrusted thereon, and weighing these materials as well as the probe. A comparison of the weight of the probe itself before and after the test makes it possible to assess the corrosive nature of the liquid, while the weight of the materials encrusted on the probe during the test is a measure of the encrusting nature of the liquid. These known methods have the disadvantage of being slow and rather imprecise, and they are incapable of providing an instantaneous indication of the surface condition of an installation in which the liquid is being treated, stored or conveyed.

It has also been proposed to monitor the corrosive character of liquids circulating in metallic installations by measuring the variation with time of the electrical resistance of a probe dipped in the liquid. This is disclosed in the periodical *Corrosion*, published by the National Association of Corrosion Engineers, Volume 14, March 1958, at pages 155t to 158t. While this known process permits precise, instantaneous and continuous monitoring of the corrosive nature of the liquid, it does not, however, make it possible to monitor the formation of crusts or of sediments on the walls of the installation. Furthermore, it suffers from the disadvantage of requiring precalibrated, expensive and fragile probes, which have to be replaced periodically.

It has also been proposed to monitor the formation of deposits of crusts on a wall in contact with a liquid, for example the wall of a heat exchanger, by measuring the variation, with time, of the temperature of the wall by means of a thermocouple seated in the wall, as disclosed in the periodical *Chemical Engineering Progress*, July 1975, Volume 71, No. 7, at pages 66 to 72. However, this known method does not lend itself to monitoring the corrosive nature of the liquid. Furthermore, it suffers from the disadvantage that it is greatly subject to variations in temperature of the medium in contact with the wall.

U.S. Pat. No. 3,612,998 issued to B. G. Turner et al on Oct. 12, 1971, proposes a process for detecting corrosion brought about by an electrokinetic phenomenon caused by the passage of a liquid at high velocity near a metallic component, which process consists of measuring the electric current generated by the continuous dissolution of the metallic component in the liquid under the action of the electrokinetic phenomenon.

This known process has the disadvantage that it is only applicable to a particular type of corrosion caused by the flow of liquids at very high velocity. It is not capable of detecting any other type of corrosion such as, for example, that which is inherent in the corrosiveness of soft waters, or of detecting erosion or encrusting. It has the additional disadvantage that it is not responsive to the surface condition of the metallic component and consequently it does not make it possible to assess the effect of the corrosion on the metallic component.

SUMMARY OF THE INVENTION

It is therefore an object of the present invention to rapidly and precisely monitor, at one and the same time, the action which a liquid exerts on the corrosion, the erosion and the encrusting of a metallic installation.

This and other objects of the invention are achieved by a process for monitoring the corrosive, erosive and/or encrusting nature of a liquid with respect to a metallic installation, according to which process a metallic probe is immersed in the liquid, and an electrical characteristic of the double layer of the probe, which is representative of the surface condition of the probe, is measured.

As used herein in connection with the present invention, the term liquid signifies an electrolyte solution or suspension, such as water, an aqueous solution of sodium chloride, an aqueous solution of sodium hydroxide, or a slurry.

The term double layer of the probe means the interfacial zone between the probe and the liquid. As is known, per se, this interfacial zone can be treated as similar, or equated, to a capacitor whose thickness is of the order of the dimensions of the ionic atmosphere, as described in the text, John O'M. Bockris and Amulya K. N.

Reddy, MODERN ELECTROCHEMISTRY, Volume 2, pages 629-30, Plenum Press, New York (1970).

The electrical characteristic of such double layer of the probe must be so chosen that it is representative of its surface condition, for example its roughness. As the electrical characteristic of the double layer of the probe it is possible, for example, to measure, in a manner which is in itself known, the faradiac rectification or, preferably, the differential capacitance of the double layer of the probe.

In the process according to the invention, the probe is made of the same material as the installation and is preferably machined so as to present approximately the same original surface condition as the installation. In this way, the change in the surface condition of the probe in contact with the liquid is representative of the effective change in the surface condition of the installation in which the liquid is treated.

In the process according to the invention, the probe is advantageously located in a critical zone of the installation, which is particularly affected by the liquid from the standpoint of corrosion, erosion or encrusting, for example in a bend or in a constricted zone of a pipeline, at the bottom of an enlarged zone of a pipeline through which a liquid containing solid materials in suspension flows, or along the wall of a heat exchanger or a crystallizer.

We have found that a variation of the electrical characteristic of the double layer of the probe relative to its original value indicates a change in its surface condition; this change can consist, for example, of a change in its roughness caused by corrosion or erosion, or of the formation of a deposit, which may be an encrusting or scaling deposit, on the surface of the probe. On comparing the measured magnitude of the electrical characteristic of the probe with the values recorded in the case of a standard probe subjected to the same test conditions, it is possible to determine the change in the surface condition of the probe and hence that of the wall of the installation, in the vicinity of which the probe is located. To compare the measured characteristic of the probe with the corresponding values of the standard, it is possible, with advantage, to use a diagram which shows the surface condition of the standard corresponding to each value of the characteristic of the double layer of the standard.

According to a preferred embodiment of the process of the invention, the differential capacitance of the double layer of the probe and the electrical resistance of a cell defined by this probe and an auxiliary electrode located in the liquid near the probe, are recorded simultaneously.

This embodiment of the invention has the advantage of distinguishing, with great precision, the formation of corrosion or erosion, on the one hand, and the formation of crusts or sedimentation on the surface of the probe, on the other hand. It has in fact been found in practice that an increase in the roughness of the surface of the probe causes a corresponding increase in the differential capacitance of the double layer and a reduction, sometimes not very noticeable, in the resistance of the measuring cell, while the formation of a dielectric deposit on the surface of the probe simultaneously causes a reduction in the capacitance of the double layer and a significant increase in the resistance of the measuring cell.

To carry out the process according to the invention, use is made of an electrochemical measuring cell composed of a probe as defined above and an auxiliary electrode connected to a device for measuring an electrical characteristic of the double layer of the probe, which characteristic is representative of the surface condition of the probe.

In devices according to the invention, the probe is produced as described above, from the same metal or alloy as the installation which is to be monitored.

The auxiliary electrode can be made of the same material as the probe or from a different material, for example a metal or an alloy which is nobler than the metal or alloy of the probe. For example, in the case of a probe of cast iron or of ordinary steel, the auxiliary electrode can be made of cast iron, of ordinary steel or, as a variant, of stainless steel.

The respective dimensions and the shape of the probe and of the auxiliary electrode are selected in accordance with the nature and the temperature of the liquid. In practice, the probe must be sufficiently large for its structure and its surface condition to be representative of the wall of the installation to be monitored. However, it is important to keep the ratio of the surface area of the probe to that of the auxiliary electrode from exceeding a value above which the capacitance of the double layer of the auxiliary electrode affects the measurement. In general terms, probes which are very suitable for use in the presence of water have a surface area which is substantially between 10 and 1,000 $mm^2$.

The device according to the invention is furthermore equipped with a measuring component which is in itself known for measuring an electrical characteristic of the double layer of the probe, preferably a component for measuring the differential capacitance of the double layer. It is advantageous to use a measuring bridge such as a Wien bridge, a Schering bridge or a Wayne Kerr bridge.

The device according to the invention can be designed to be seated inside an installation which is intended to contain a liquid and which it is desired to monitor during use.

According to an advantageous embodiment of the device of the invention, the probe or the auxiliary electrode constitutes a removable wall element of the installation. This embodiment of the invention facilitates positioning and removal of the measuring cell. It furthermore makes it possible to locate the probe with precision in the immediate vicinity of the surface of the wall to be monitored.

According to an advantageous variant of this embodiment of the invention, the auxiliary electrode forms a removable wall element of the installation and the probe is seated in a removable manner in a slot of the auxiliary electrode. This variant of the invention has the advantage of being compact and furthermore facilitates positioning and extracting the measuring cell as well as replacing the probe.

According to a preferred embodiment of the device of the invention, the auxiliary electrode consists of the installation itself.

According to another particular embodiment of the device according to the invention, the measuring component is connected to a recording component coupled to a component which signals the occurrence of a predetermined critical value of the electrical characteristic being measured; this critical value corresponds to a particular surface condition of the probe, determined beforehand by means of a standard probe subjected to the same working conditions as the installation which it is desired to monitor. This critical value can correspond, for example, to a state of corrosion which is dangerous from the point of view of good maintenance of the installation, or to a degree of scaling which is excessive for satisfactory functioning of the installation.

The process and the device according to the invention have the advantageous characteristic of allowing precise, continuous and automatic monitoring of the change in the surface condition of a metallic installation in contact with a liquid. They provide the additional advantage of being sensitive to small variations in the surface condition of the metallic installations, especially to the start of corrosion or of local encrusting.

The invention is particularly adapted for monitoring and controlling the functioning of metallic installations or apparatus in contact with liquids, in order to avoid excessive and harmful corrosion, erosion and/or encrusting of these installations. Generally the process and the device of this invention may be used to act on a parameter controlling the functioning of the installation, said parameter influencing on the corrosive, erosive and/or encrusting action of the liquid on the installation. For this aim, it is sufficient to control continuously or intermittently the magnitude of said parameter in response to the instantaneous magnitude of the electrical characteristic of the double layer of the probe immersed in the liquid. Such a control may be carried out for example by hand, with reference to the measured numerical value of the characteristic of the double layer.

In a modified embodiment, the device according to the invention may be connected to an automatic control system of a parameter acting on the functioning of the installation, said parameter being selected among those which influence on the corrosive, erosive and/or encrusting action of the liquid on the installation. In this particular embodiment, said automatic control system is generally adapted to act on said parameter in response to a signal transmitted from the device according to the invention and representative of the instantaneous magnitude of the selected characteristic of the double layer of the probe of said device, in order to bring said magnitude back to a preselected value.

Suitable parameters are for example the temperature and the pressure of the liquid handled in the installation, its flow through the installation, the amount of a substance dissolved or dispersed in the liquid, the pH of the liquid, the amount of an encrusting inhibitor in the liquid, or the temperature of the wall of the installation.

The invention can be applied to every installations or apparatus wherein a liquid is handled, for example a storage tank, a pipe, a pressure vessel, a heat exchange, etc . . . In the present specification heat exchanger means any installation or apparatus especially adapted to bring about a heat transfer between two fluids which have different temperatures, for example a cooling tower, a heater or an evaporator.

DESCRIPTION OF THE PREFERRED EMBODIMENTS

Figure 1:
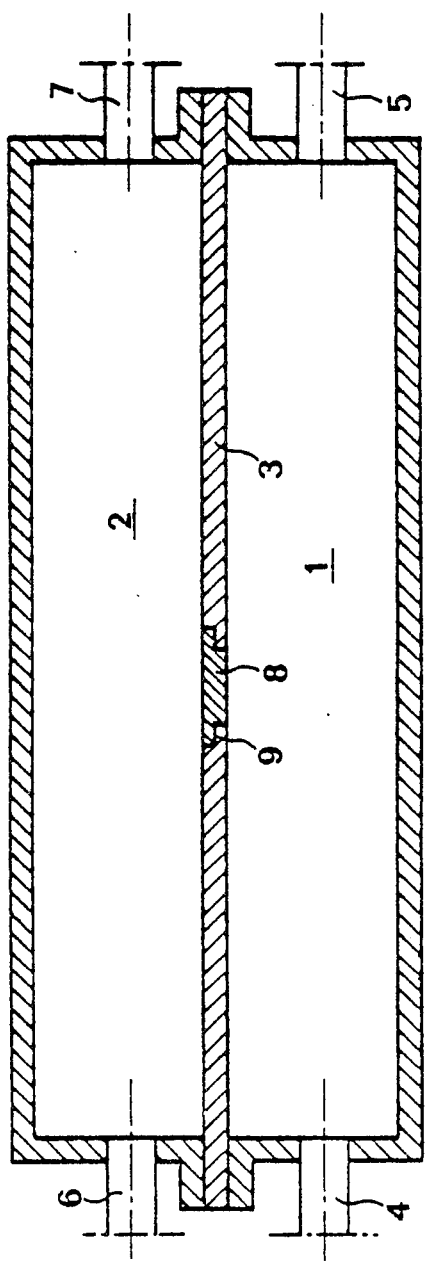
FIG. 1 is a schematic view, in longitudinal section, of a test cell used to carry out the tests described below.

A measuring cell which simulates a heat exchanger was used for carrying out the tests to be described below. The cell, shown schematically in FIG. 1, is made of stainless steel and presents two sub-chambers 1 and 2 isolated from one another by a common partition 3. Chamber 1 is provided, at its opposite ends, with tubes 4 and 5 by means of which it is integrated into a circuit of encrusting water at a defined temperature, and chamber 2 is provided with tubes 6 and 7 for connecting it to a circuit of hot oil maintained at a defined temperature. The common partition 3 thus acts as a heat exchange wall of a heat exchanger through which two fluids at different temperatures flow. An orifice was formed in the common wall 3 of the cell, in order to seat therein a circular probe 8 made of mild steel. An insulating gasket 9 of polyvinylidene fluoride ensures the creation of a fluid-tight seal between the probe 8 and the partition 3 and insulates them electrically from one another.

In the measuring cell of FIG. 1, the process according to the invention was carried out in order to monitor the action of the encrusting water flowing in chamber 1 on the mild steel probe 8. For this purpose, the internal surface of all the walls of chamber 1 was used as the auxiliary electrode and was connected, as was the probe 8, to a capacitance measuring bridge of the Wayne-Kerr type.

1st series of tests

The tests relating to Examples 1 to 4, which follow, were carried out with a mild steel probe 8 having a surface area of 20 mm$^2$. In each of these tests, water from the Brussels, Belgium town mains were passed through chamber 1 of the cell at a constant velocity of 5 cm/sec and the differential capacitance of the double layer of the probe and the internal resistance of the measuring cell were recorded periodically by means of the Wayne-Kerr measuring bridge. The results of the four tests have been set out in Tables I to IV below and in the diagrams of FIGS. 2 to 5. In the 3rd and 5th columns of each table, the capacitance and the resistance, respectively, are expressed as a percentage of their maximum values recorded during the test in question. In each of the diagrams of FIGS. 2 to 5, all scales are logarithmic, the abscissa scale represents the time from the start of the test, in minutes, the left-hand ordinate scale represents the differential capacitance of the double layer as a percent of its maximum value during the test in question and the right-hand ordinate scale represents the resistance of the measuring cell as a percent of its maximum value during the test in question. The solid lines represent the change in the differential capacitance of the double layer with time and the broken lines represent the change in the resistance of the measuring cell with time.

EXAMPLE 1

Probe 8 was carefully polished and then placed in the measuring cell as described above. During the test, the oil was kept at a temperature of the order of 76° C. in chamber 2 and the water circulated in a closed circuit through the chamber 1 at a temperature of the order of 14° C. During the test, the temperature of the oil and the temperature of the water in the cell did not vary by more than one degree relative to the above-mentioned values. The results of the test are set out in Table 1, below, and in the diagram of FIG. 2.

TABLE I

| Time | Capacitance | | Resistance | |
|---|---|---|---|---|
| (minutes) | (μF) | (%) | (Ω) | % |
| 4 | 0.065 | 0.97 | 2679.52 | 96.36 |
| 22 | 0.127 | 1.90 | 2208.48 | 79.42 |
| 35 | 0.160 | 2.39 | 2068.25 | 74.37 |
| 51 | 0.142 | 2.12 | 2088.55 | 75.10 |
| 70 | 0.161 | 2.40 | 2037.48 | 73.27 |
| 121 | 0.180 | 2.69 | 2064.83 | 74.25 |
| 1,080 | 3.902 | 58.23 | 1265.34 | 45.50 |
| 1,525 | 6.701 | 100.00 | 1492.09 | 53.66 |
| 2,523 | 2.807 | 41.89 | 1655.08 | 59.52 |
| 2,944 | 3.330 | 49.69 | 1463.70 | 52.63 |
| 6,879 | 1.440 | 21.49 | 2307.0 | 82.96 |
| 7,263 | 1.390 | 20.74 | 2345.7 | 84.35 |
| 8,282 | 1.076 | 16.06 | 2574.0 | 92.56 |
| 12,602 | 0.536 | 8.00 | 2780.8 | 100.00 |

At the end of the test, it was found that encrusted zones, adjoining heavily corroded zones with a rough surface, were present on the probe.

Figure 2:
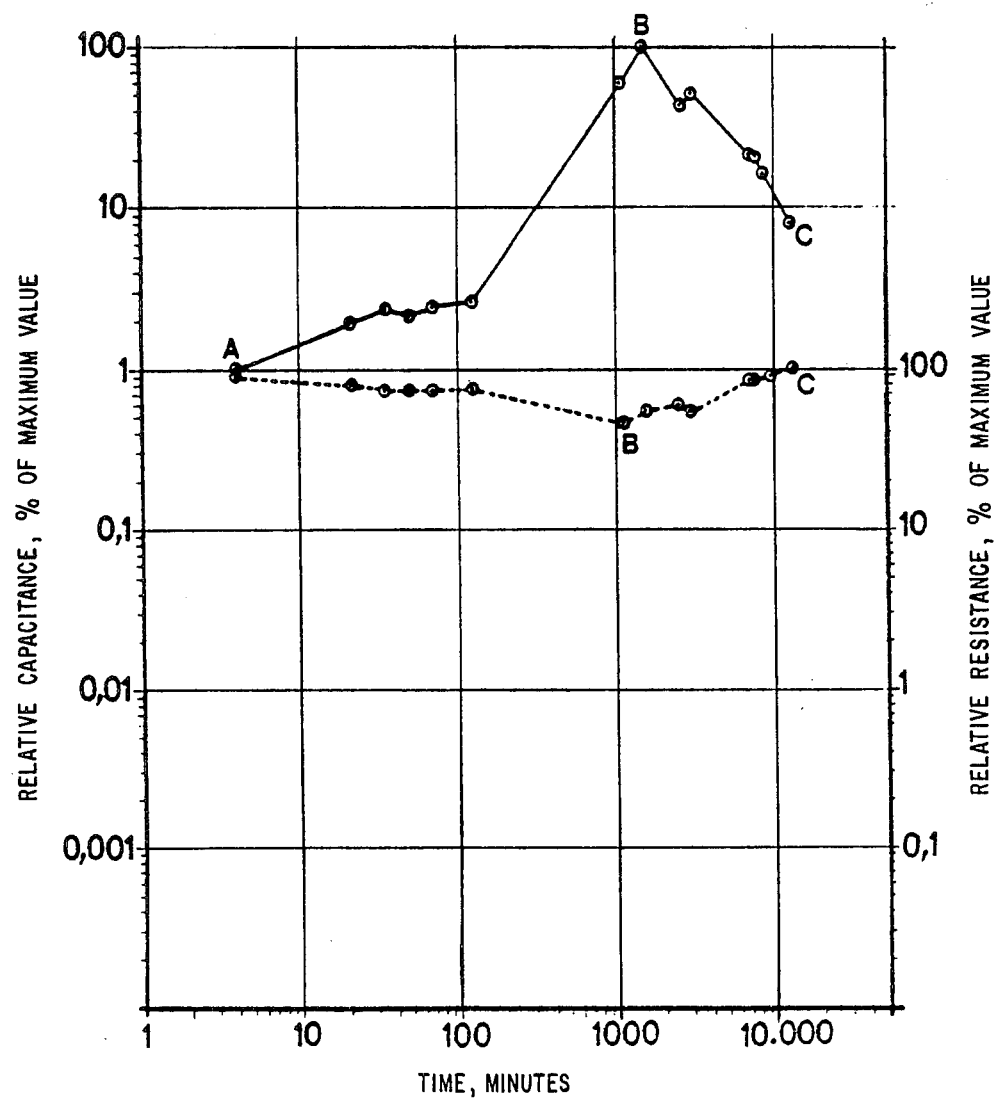
FIGS. 2 to 6 are diagrams illustrating the results of those tests.

Table I and the diagram of FIG. 2 are in agreement with these observations. In the diagram, the zone AB in fact corresponds to substantial corrosion of the probe whilst zone BC corresponds to progressive and substantial encrusting of the surface of the probe.

EXAMPLE 2

After having removed the deposit formed on the probe during the test of Example 1, the probe, in this sate, was replaced in the measuring cell, without polishing it. The test of Example 1 was then repeated, but this time with the oil in chamber 2 of the cell at a temperature of 76° C. and the water in chamber 1 at a temperature of 19° C. The results of the test are set out in Table II, below, and in the diagram of FIG. 3.

TABLE II

| Time | Capacitance | | Resistance | |
|---|---|---|---|---|
| (minutes) | (μF) | (%) | (Ω) | (%) |
| 9 | 2.174 | 100.0 | 1162.3 | 17.6 |
| 20 | 1.699 | 78.2 | 1378.7 | 20.8 |
| 31 | 1.843 | 84.8 | 1209.7 | 18.3 |
| 49 | 1.954 | 89.9 | 997.6 | 15.1 |
| 62 | 1.728 | 79.5 | 1343.4 | 20.3 |
| 122 | 1.984 | 91.3 | 1166.0 | 17.6 |
| 482 | 1.299 | 59.8 | 1525.2 | 23.1 |
| 1,445 | 0.670 | 30.8 | 2029.9 | 30.7 |
| 1,923 | 0.589 | 27.1 | 2165.3 | 32.7 |
| 2,884 | 0.305 | 14.0 | 2957.7 | 44.7 |
| 3,363 | 0.114 | 5.2 | 4183.0 | 63.2 |
| 4,323 | 0.0396 | 1.8 | 6351.6 | 96.0 |
| 4,803 | 0.0422 | 1.9 | 6614.0 | 100.0 |

Figure 3:
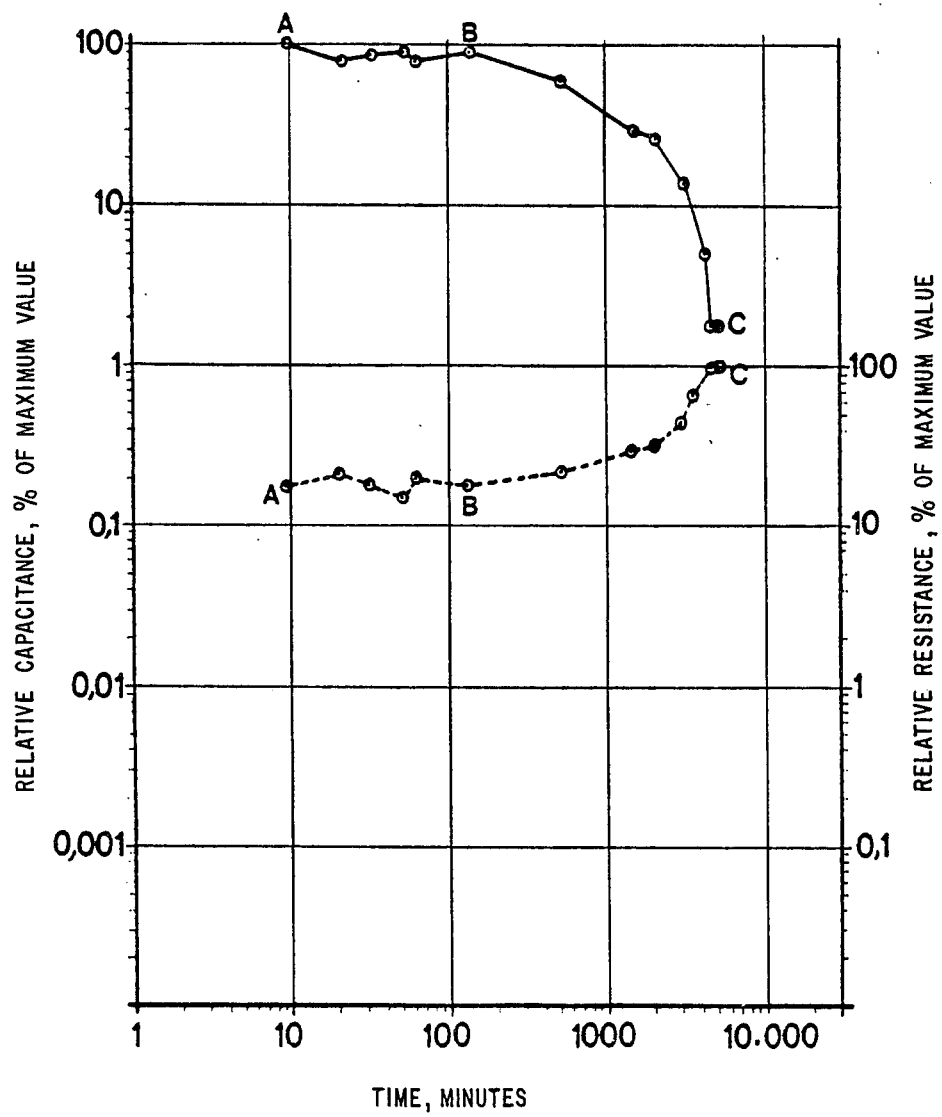

Inspection of the diagram of FIG. 3 shows that, above all, encrusting took place on the non-polished probe (zone BC of the diagram), while corrosion is less extensive than in the case of Example 1 and is accompanied by a simultaneous encrusting of the surface of the probe (zone AB of the diagram).

These results were confirmed by a visual observation of the probe at the end of the test. The probe was covered with a more homogeneous adhering deposit than in Example 1. After having removed the deposit, the surface of the probe appeared a little rougher than at the start of the test.

EXAMPLE 3

The test of Example 2 was repeated after having removed the deposit formed on the probe, but without repolishing the latter. The following operating conditions were used: oil temperature: 95° C.; water temperature: 60° C.

Figure 4:
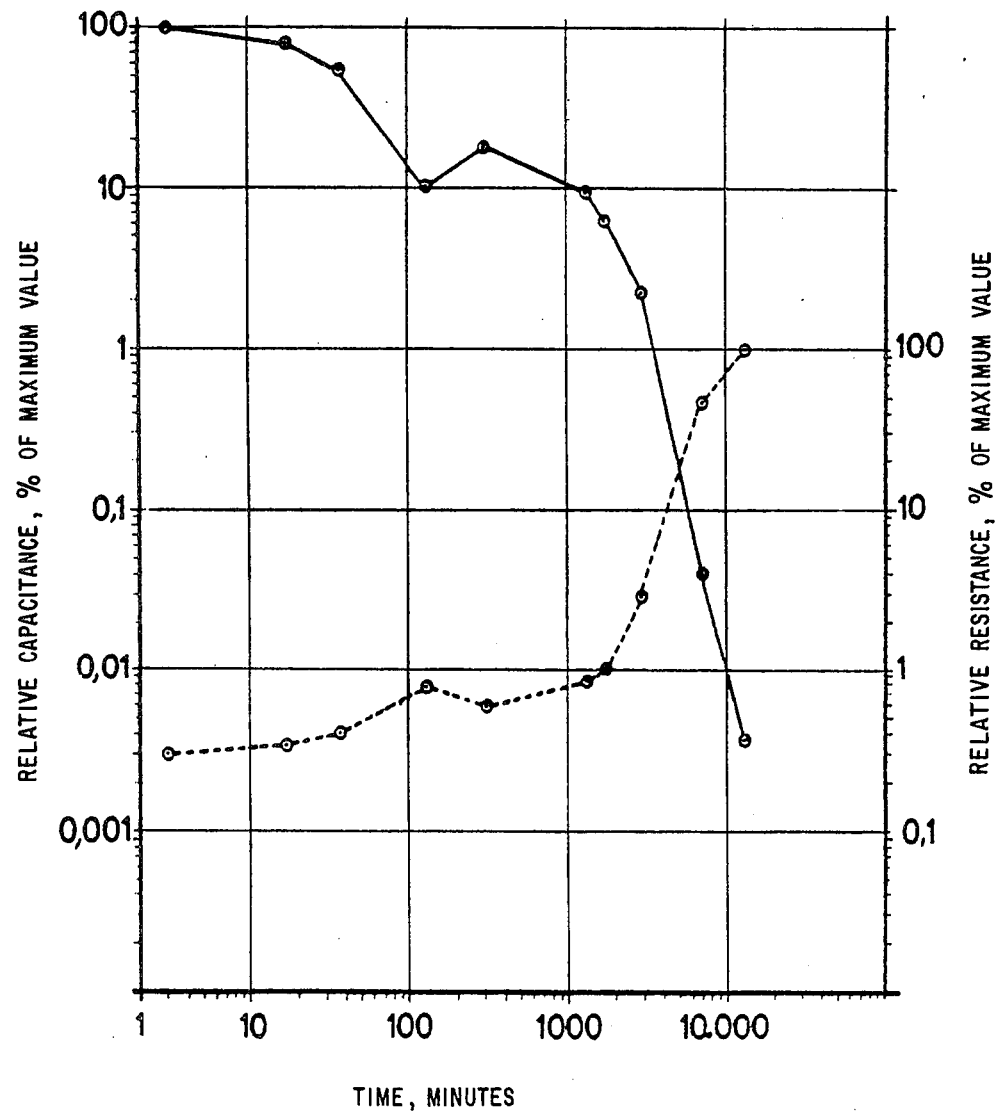

The results of the test are set out in Table III below, and in the diagram of FIG. 4, which show, according to the invention, that during this test the probe underwent virtually no corrosion but was almost exclusively subject to encrusting. These results were confirmed by a visual observation of the probe at the end of the test; the probe appeared covered with a thick adherent deposit. After removing the deposit, the roughness of the surface of the probe appeared to be unchanged compared to its roughness at the start of the test.

TABLE III

| Time | Capacitance | | Resistance | |
|---|---|---|---|---|
| (minutes) | (μF) | (%) | (Ω) | (%) |
| 2 | 6.050 | 100 | 504.01 | 0.298 |
| 17 | 4.788 | 79.1 | 597.23 | 0.354 |
| 37 | 3.331 | 55.1 | 678.98 | 0.403 |
| 132 | 0.626 | 10.3 | 1,323.10 | 0.785 |
| 302 | 1.087 | 18.0 | 1,006.85 | 0.597 |
| 1,293 | 0.580 | 9.6 | 1,413.83 | 0.839 |
| 1,683 | 0.383 | 6.3 | 1,702.42 | 1.01 |
| 2,883 | 0.135 | 2.23 | 4,995.00 | 2.96 |
| 7,203 | 0.0025 | 0.0413 | 80,000.00 | 47.46 |
| 13,143 | 0.00023 | 0.0037 | 168,575.40 | 100.0 |

EXAMPLE 4

After having removed the deposit formed on the probe during the test of Example 3, the probe was replaced in the cell, without polishing it. The test of Example 3 was then repeated, but regulating the pH of the water to 6.5 and incorporating into the water an encrusting inhibitor known by name of COBF 3 (from the COPEF firm) and consisting of a mixture of polyphosphate, a zinc salt and a dispersing agent of the phosphonate type. The encrusting inhibitor was supplied at the rate of 150 mg per liter of water for the first five days of the test (7,200 minutes) and then at the rate of 60 mg per liter of water up to the end of the test.

Figure 5:
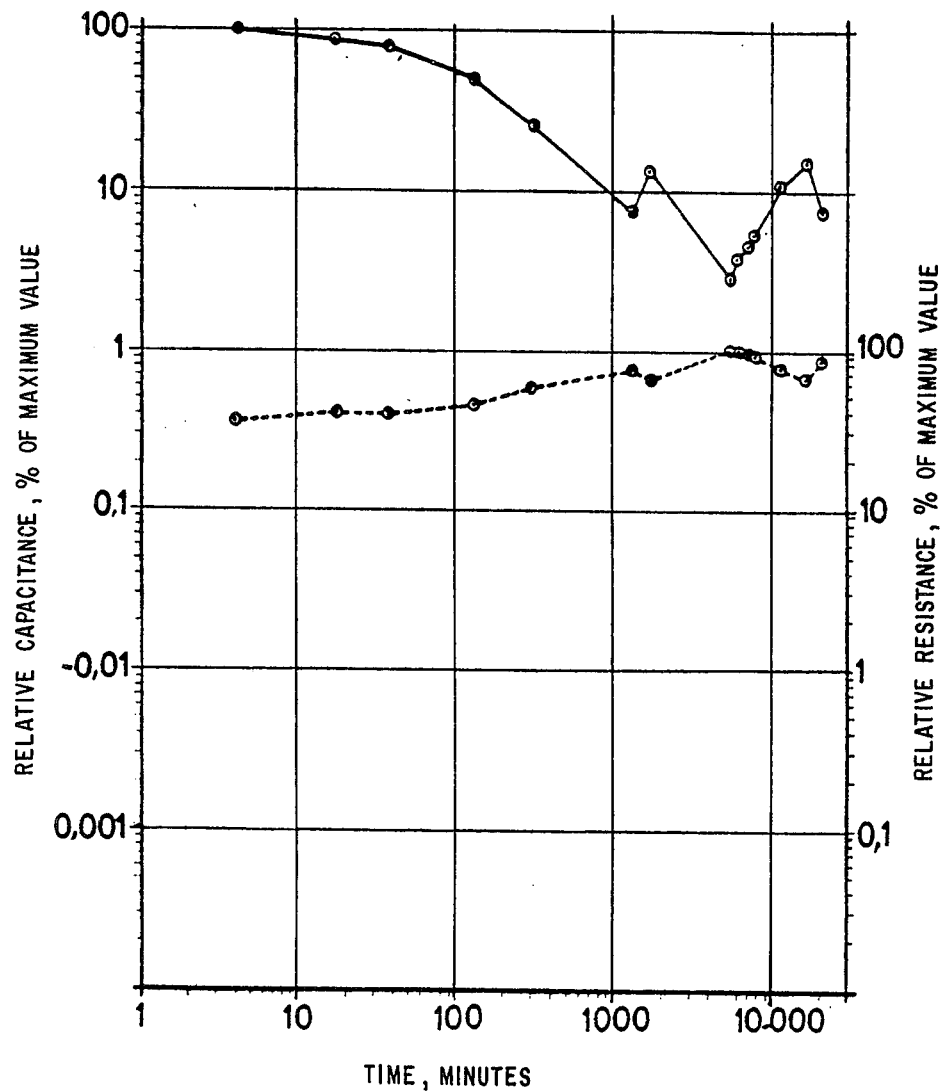

The results of the test are set out in Table IV, below, and in the diagram of FIG. 5.

TABLE IV

| Time | Capacitance | | Resistance | |
|---|---|---|---|---|
| (minutes) | (μF) | (%) | (Ω) | (%) |
| 4 | 9.971 | 100.0 | 343.3 | 36.08 |
| 17 | 8.771 | 87.97 | 383.4 | 40.30 |
| 37 | 7.573 | 75.95 | 378.6 | 39.79 |
| 132 | 4.931 | 49.45 | 426.9 | 44.87 |
| 302 | 2.592 | 26.00 | 549.8 | 57.79 |
| 1,323 | 0.734 | 7.36 | 710.8 | 74.71 |
| 1,743 | 1.329 | 13.33 | 628.0 | 66.01 |
| 5,643 | 0.271 | 2.72 | 991.4 | 100.0 |
| 6,063 | 0.362 | 3.63 | 946.2 | 99.45 |
| 7,083 | 0.445 | 4.46 | 900.0 | 94.60 |
| 7,503 | 0.536 | 5.38 | 881.3 | 92.63 |
| 11,703 | 1.018 | 10.21 | 742.9 | 78.08 |
| 17,283 | 1.495 | 14.9 | 629.4 | 66.16 |
| 21,543 | 0.756 | 7.58 | 826.3 | 86.85 |

A comparison of the results of Examples 3 and 4 permits the conclusion, according to the invention, that the presence of an encrusting inhibitor in the water did not make the corrosion of the probe more severe, but on the other hand provided the beneficial result of substantially reducing encrusting.

This was confirmed by visual observation of the probe at the end of the test of Example 4. The probe showed a deposit which adhered only slightly and was thinner than at the end of the test of Example 3. Furthermore, after removing the deposit, the metallic surface of the probe appeared unchanged compared to its condition at the start of the test.

Second series of tests

The tests of the above-mentioned Examples 2, 3 and 4 were repeated successively, with a mild steel probe of 200 mm$^2$ surface area, which had an initial rough surface, and the differential capacitance of the double layer of the probe during each test was recorded. At the end of each test, the probe was removed from the measuring cell, the deposit formed on the probe was removed and weighed, and its calcium content was determined.

For each test, the characteristics of the deposit formed on the probe as well as the differential capacitance of the double layer at the end of the test, expressed as a percent of its maximum value during the test, were set out in Table V. The diagram of FIG. 6 restates the results of Table V. In this diagram, the abscissa scale represents the weight of calcium of the deposit, expressed in g per m$^2$ of surface area of the probe, and the ordinate scale indicates the differential capacitance of the double layer at the end of the test, expressed as a percent of its maxium value during the test.

Figure 6:
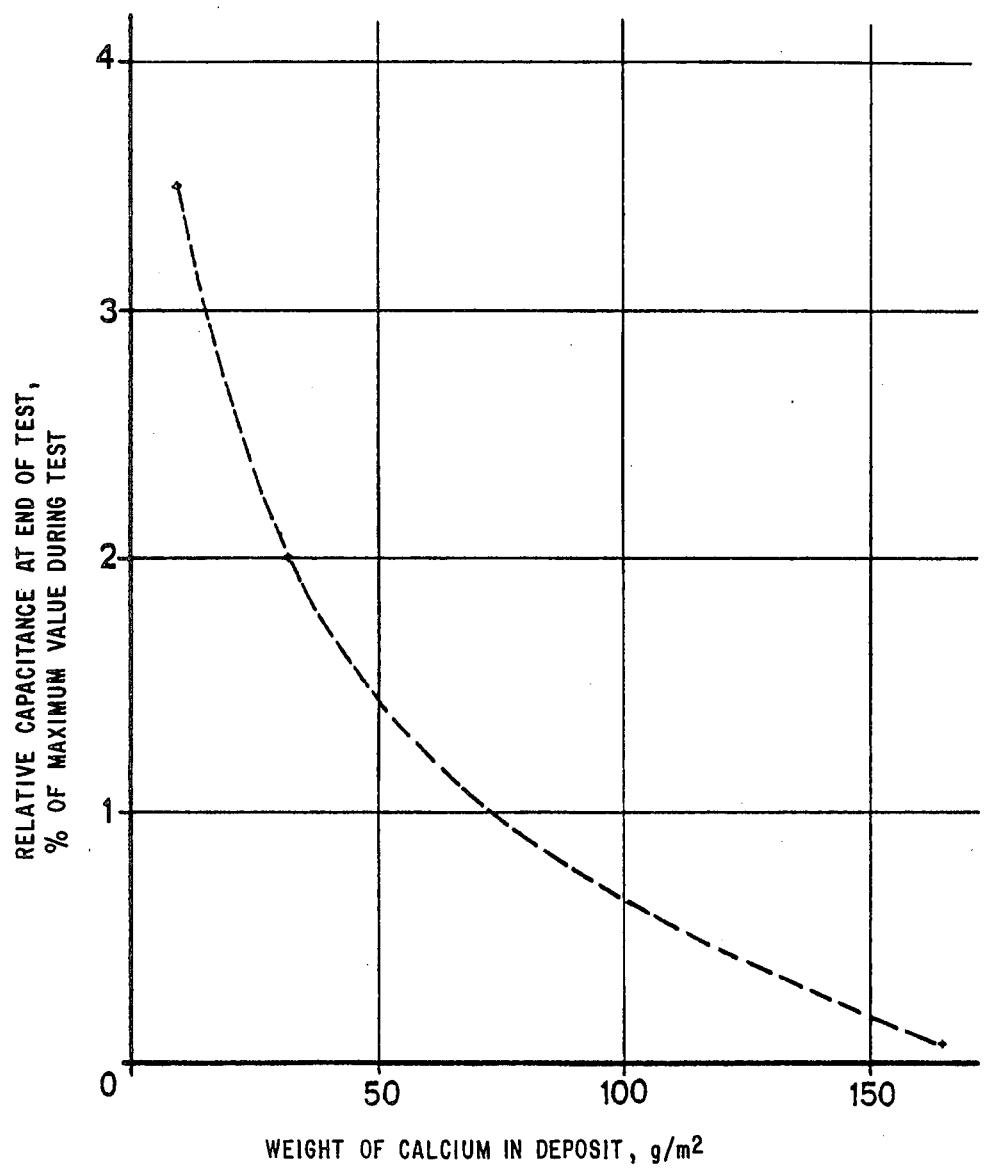

Inspection of Table V and of the diagram of FIG. 6 shows that the process according to the invention makes it possible to rapidly determine the extent of encrusting from a measurement of the differential capacitance of a metallic probe dipped into the water.

TABLE V

| Test (No. | Capacitance (%) | Weight of the deposit (g/m$^2$) | Weight of calcium (g/m$^2$) |
|---|---|---|---|
| 1 | 3.5 | 140 | 9.4 |
| 2 | 0.0589 | 562 | 165.2 |
| 3 | 2.61 | 115 | 32.0 |

Figure 7:
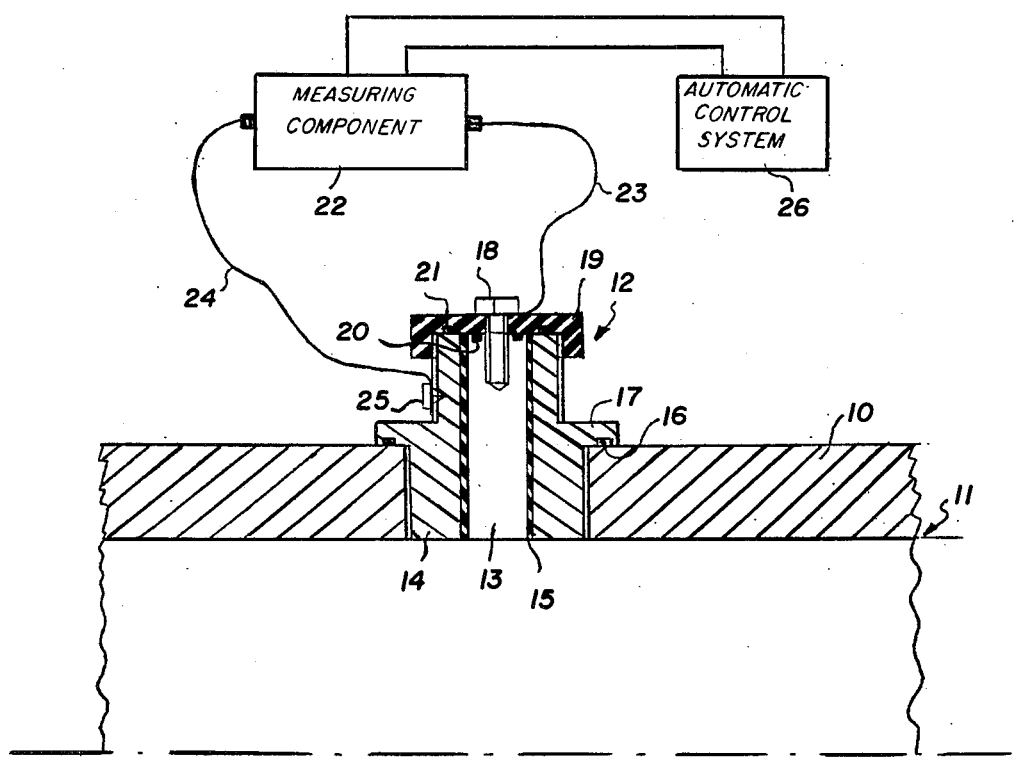
FIG. 7 is a partial schematic view, in axial section, of an installation equipped with a device according to the invention.

We have shown on FIG. 7 a particular embodiment of the device of this invention, adapted to monitor the corrosion, erosion and/or encrustation occuring on a wall 10 of an installation 11 for the handling of a liquid, for example the wall of a carbonating tower for the ammonia soda process such as described in the book "Manufacture of Soda" by Te-Pang Hou, Hafner Publishing Company (1969).

According to the invention this device includes an electrochemical measuring cell 12 comprising a cylindrical metallic probe 13 axially engaged in a tubular auxiliary electrode 14. The probe 13 and the auxiliary electrode 14 are made of the same material as the wall 10 of the installation 11, for example of cast iron, and they are electrically insulated from each other by an insulating film 15 made for example of polytetrafluorethylene.

The tubular auxiliary electrode 14 has a lower cylindrical portion which is screwed in a corresponding threaded bore through the wall 10 of the installation 11, an annular sealing joint 16 being compressed between said wall 10 and an annular shoulder 17 of the tubular electrode 14.

The cylindrical probe 13 is removably supported in the tubular auxiliary electrode 14 by means of a metallic screw 18 passing though a cap 19 screwed on the upper cylindrical portion of the auxiliary electrode 14. Said cap 19 is made of an electrically non-conducting material, for example polytetrafluorethylene, in order to maintain the probe 13 insulated from the auxiliary electrode 14. Two annular sealing joints 20 and 21 are interposed between the cap 19 and respectively the probe 13 and the auxiliary electrode 14.

The probe 13 and the auxiliary electrode 14 are connected separately to a measuring component 22 through conducting leads 23 and 24 connected respectively to the screw 18 of the probe 13 and to a screw 25 of the auxiliary electrode 14.

The measuring component 22 is a component known per se for measuring the differential capacitance of the double layer of the probe when a liquid is handled in the installation 11. It is advantageously adapted to measure further the electrical resistance of the measuring cell 12, when both electrodes 13 and 14 contact a liquid handled in the installation 11.

The measuring component 22 may be advantageously a capacitance measuring bridge commonly used in the art, for example a Wien bridge, a Schering bridge or a Wayne Kerr bridge.

According to the invention, the measuring component 22 may be connected to an automatic control system 26 of a parameter of the functioning of the installation 11, said parameter influencing the corrosive, erosive and/or encrusting action of the liquid on the wall 10 of the installation 11. The automatic control system 26 may be for example a thermostat controlling the temperature of the liquid handled in the installation 11, or a motorized valve controlling the flow of the liquid through the installation.

In a modified embodiment, not shown, of the device of FIG. 7, the auxiliary electrode 14 may be the wall 10 itself of the installation 11. The screw 25 is then attached directly to the wall 10 of the installation 11.

In another modified embodiment, not shown, of the device of FIG. 7, the auxiliary electrode 14 may be made of a metal or alloy which is not subjected to corrosion, erosion and encrustation when used in the installation 11, for example of stainless steel. In this modified embodiment, it is necessary to provide an electrically non conducting film between the electrode 14 and the wall 10, in order to insulate them from each other.

It will be understood that the above description of the present invention is susceptible to various modifications, changes and adaptations, and the same are intended to be comprehended within the meaning and range of equivalents of the appended claims.

What is claimed is:

1. Process for monitoring the corrosive, erosive and/or encrusting nature of a liquid with respect to a metallic installation, comprising: immersing a metallic probe into the liquid whereby a double layer is created at the interface between the probe and the liquid; immersing an auxiliary electrode into the liquid near the probe so that the auxiliary electrode is electrically insulated from the probe and measuring the differential capacitance of the double layer and the electrical resistance between the probe and the auxiliary electrode, which are representative of the surface condition of the probe.

2. Process as defined in claim 1 wherein said step of immersing is carried out by placing the probe near a surface of the installation, in contact with the liquid.

3. Process as defined in claim 2 wherein the probe is made of the same material as the installation.

4. Process as defined in claim 2 wherein the probe has substantially the same surface condition as the surface of the installation near which it is placed.

5. Process as defined in claim 2 wherein the probe is an element of the surface of the installation near which it is placed.

6. Process as defined in claim 5 wherein the probe is a removable element of the surface of the installation near which it is placed.

7. Process as defined in claim 1 wherein the installation is a pipeline for the liquid.

8. Process as defined in claim 1 wherein the installation is a heat exchanger.

9. Process as defined in claim 8 wherein the installation includes an evaporator for the liquid.

10. Process as defined in claim 1 wherein the liquid is water.

11. Process as defined in claim 1 wherein the liquid is an aqueous solution of sodium hydroxide.

12. Device for monitoring the corrosive, erosive and/or encrusting nature of a liquid with respect to a metallic installation, comprising: an electrochemical measuring cell constituted by a metallic probe and an auxiliary electrode arranged to contact the liquid to create a double layer at the interface between the probe and the liquid; and a component connected to said cell for measuring the differential capacitance of the double layer and the electrical resistance of said cell, which are representative of the surface condition of the probe.

13. Device as defined in claim 12 wherein said probe is made of the same metal as the installation.

14. Device as defined in claim 12 wherein at least one of said probe and said auxiliary electrode forms a removable wall element of the installation.

15. Device as defined in claim 12 wherein said auxiliary electrode forms a removable wall element of the installation and is provided with a slot, said probe is engaged in a removable manner in said slot of said auxiliary electrode; and said cell further comprises electrical insulation interposed between said probe and said electrode.

16. Device as defined in claim 12 wherein said auxiliary electrode is made of the same material as the installation.

17. Device as defined in claim 16 wherein the installation constitutes said auxiliary electrode.

18. Device as defined in claim 12 further comprising a signalling component connected to said measuring component for signalling a predetermined critical value of at least one of the above-mentioned capacitance and electrical resistance.

* * * * *